United States Patent
Kawamura et al.

(10) Patent No.: US 6,664,440 B2
(45) Date of Patent: Dec. 16, 2003

(54) DISPOSABLE UNDERGARMENT WITH SWEAT-ABSORBENT PAD IN WAISTBAND

(75) Inventors: Kouji Kawamura, Kagawa-ken (JP); Yoshio Ono, Kagawa-ken (JP)

(73) Assignee: Uni-Charm Corporation, Ehime-ken (JP)

(*) Notice: Subject to any disclaimer, the term of this patent is extended or adjusted under 35 U.S.C. 154(b) by 9 days.

(21) Appl. No.: 09/864,587

(22) Filed: May 24, 2001

(65) Prior Publication Data

US 2001/0049512 A1 Dec. 6, 2001

(30) Foreign Application Priority Data

May 25, 2000 (JP) ........................................ 2000-155072

(51) Int. Cl.[7] ................................................ A61F 13/20
(52) U.S. Cl. ............... 604/378; 604/385.3; 604/385.29; 604/385.01
(58) Field of Search .................. 604/385.01, 385.3, 604/378, 385.08, 385.13, 385.23, 385.26, 385.29

(56) References Cited

U.S. PATENT DOCUMENTS

| | | | |
|---|---|---|---|
| 4,804,378 A | * | 2/1989 | Shiba et al. ................. 604/367 |
| 5,246,432 A | * | 9/1993 | Suzuki et al. ........... 604/385.25 |
| 5,449,352 A | * | 9/1995 | Nishino et al. .............. 604/383 |
| 5,836,930 A | * | 11/1998 | Lantz et al. ................. 604/378 |
| 5,927,296 A | | 7/1999 | Maturaporn |
| 6,013,349 A | * | 1/2000 | Takeuchi et al. ............. 428/152 |
| 6,146,367 A | * | 11/2000 | Otsubo et al. .......... 604/385.01 |
| 6,364,863 B1 | * | 4/2002 | Yamamoto et al. ..... 604/385.27 |
| 6,393,734 B1 | * | 5/2002 | Ou .................................. 36/97 |
| 6,454,747 B1 | * | 9/2002 | Shimada et al. ............. 604/312 |

FOREIGN PATENT DOCUMENTS

| EP | 0 558 351 A1 | 3/1993 |
|---|---|---|
| JP | 5-41525 | 6/1993 |

* cited by examiner

Primary Examiner—John Rivell
Assistant Examiner—Amanda Flynn
(74) Attorney, Agent, or Firm—Butzel Long

(57) ABSTRACT

A disposable undergarment is provided on inside of a waist-opening's peripheral edge with a sweat-absorbent sheet comprising an inner layer destined to come in contact with a wearer's skin and an outer layer opposed to the inner layer. The inner layer contains hydrophobic fibers of 70~98 w % and hydrophilic fibers of at least 2 w %. The outer layer contains hydrophilic fibers of 50~100 w % of which a part extends outward from the outer layer through interstices of the hydrophobic fibers to the skin contacting surface of the inner surface.

8 Claims, 4 Drawing Sheets

DISPOSABLE UNDERGARMENT WITH SWEAT-ABSORBENT PAD IN WAISTBAND

BACKGROUND OF THE INVENTION

This invention relates to a disposable undergarment such as a disposable diaper, training pants or the like.

In paper diaper disclosed by Japanese Utility Model Application Publication No. 1993-41525A, a heat rash-proof sheet is detachably attached to inner side of the diaper along a part of a waist-opening's edge.

The heat rash-proof sheet in the diaper of prior art is made of cotton cloth and its skin contacting surface may cause uncomfortable feeling of the wearer upon absorbing of wearer s sweat.

SUMMARY OF THE INVENTION

It is an object of this invention to provide a disposable undergarment such as a disposable diaper designed so that the inner side of the waist-opening's edge may be kept dry.

According to this invention, there is provided a disposable undergarment comprising a covering member adapted to cover a wearer's crotch region, front and rear waist regions, the covering member being connected at its transversely opposite side edges so as to form a waist-opening and a pair of leg-openings, and a sweat-absorbent sheet provided on inside of the waist-opening's peripheral edge.

According to this invention the sweat-absorbent sheet comprises an inner layer destined to come in contact with wearer's skin and an outer layer opposed to the inner layer, the inner layer containing hydrophobic fibers of 70~98 w % and hydrophilic fibers of at least 2 w % while the outer layer containing hydrophilic fibers of 50~100 w % of which a part extends outward from the outer layer through interstices of the hydrophobic fibers to a skin contacting surface of the inner surface.

DETAILED DESCRIPTION OF THE PREFERRED EMBODIMENTS

Details of the disposable undergarment according to this invention will be fully understood from the description of the disposable diaper as a specific embodiment of this invention with reference to the accompanying drawings.

Figure 1:
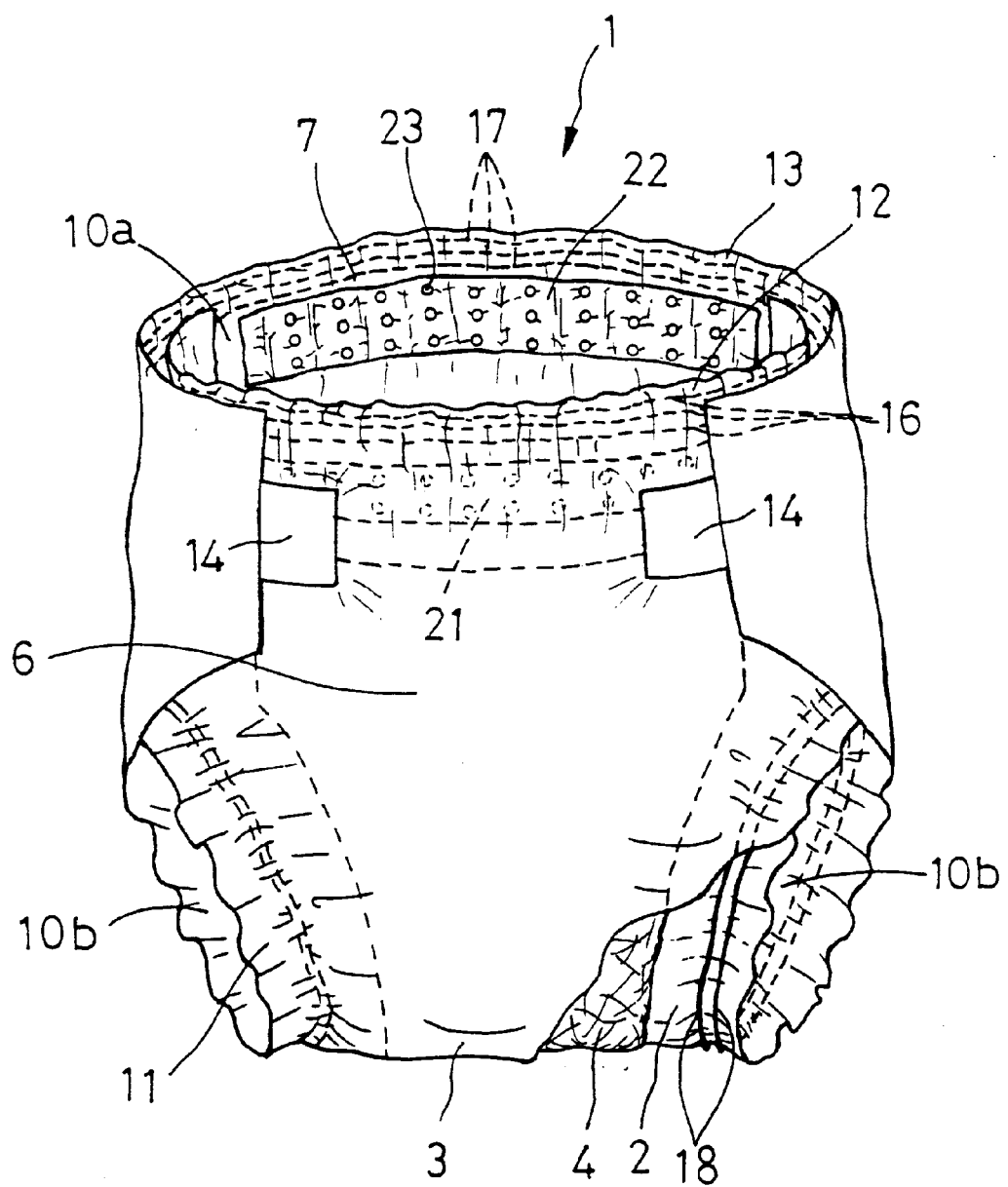
FIG. 1 is a perspective view showing a disposable undergarment (diaper) as partially broken away.
Figure 2:
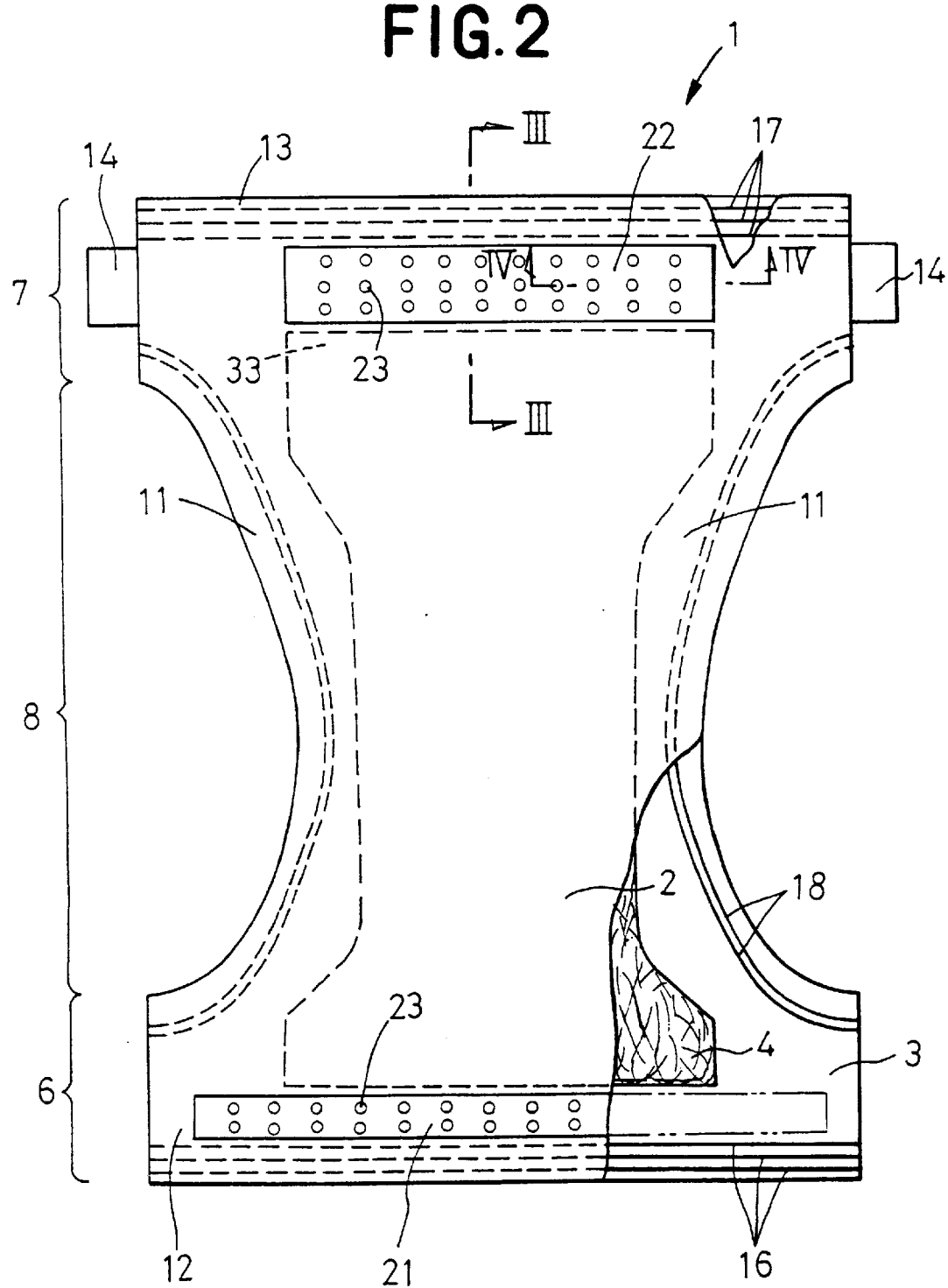
FIG. 2 is a plan view showing the diaper of FIG. 1 as developed and partially broken away.

FIG. 1 is a perspective view showing a disposable diaper 1 as put on the wearer's body and FIG. 2 is a plan view showing this diaper 1 as developed. The diaper 1 comprises a liquid-pervious topsheet 2, a liquid-impervious backsheet 3 and a body fluid absorbent core 4 disposed between these two sheets 2, 3. As will be apparent from FIG. 2, the diaper 1 is longitudinally composed of a front waist region 6, a rear waist region 7 and a crotch region 8 extending between two waist regions 6, 7 so that these regions 6~8 are adapted to cover front and rear waist regions and the crotch region, respectively, of the diaper's wearer. The top- and backsheets 2, 3 have their portions extending outward beyond a peripheral edge of the core 4 placed upon and bonded to each other to form a pair of side flaps 11 extending in the longitudinal direction and front and rear end flaps 12, 13 extending in the transverse direction orthogonal to the longitudinal direction. The side flaps 11 of the rear waist region 7 are provided with tape fasteners 14 and, in the crotch region 8, the side flaps 11 curved inwardly of the diaper 1. As shown in FIG. 1, the front and rear waist regions 6, 7 may be connected to each other along their side edges by means of these fasteners 14 to form a waist opening 10a and a pair of leg-openings 10b. The front and rear end flaps 12, 13 of the front and rear waist regions 6, 7 and the side flaps 11 in the crotch region 8 are provided with elastic members 16, 17 associated with the waist-opening and elastic members 18 associated with the respective leg-openings. The elastic members 16, 17, 18 are disposed between the top- and backsheets 2, 3 and bonded to inner surface of the topsheet 2 and/or the backsheet 3. Gathers are formed in the respective flaps 11, 12, 13 as the elastic members 16, 17, 18 associated with the waist-opening and the leg-openings contract (See Fig. 1).

As will be apparent from FIG. 2, a front sweat-absorbent sheet 21 and a rear sweat-absorbent sheet 22 are attached to inner surface of the topsheet 2 in the front and rear end flaps 12, 13, respectively. The front and rear sweat-absorbent sheets 21, 22 may be of similar construction and length thereof may be selectively dimensioned. According to the illustrated embodiment, the front sweat-absorbent sheet 21 extends substantially along the full width of the front waist region 6 and the rear sweat-absorbent sheet 22 is preferably dimensioned to be substantially equal to the width of the core in order to avoid a situation that the rear sweat-absorbent sheet 22 might overlap the front waist region 6 when the diaper 1 is worn as seen in FIG. 1. The front and rear sweat-absorbent sheets 21, 22 are formed with a plurality of vent pores 23 extending through these sheets in their thickness direction.

Figure 3:
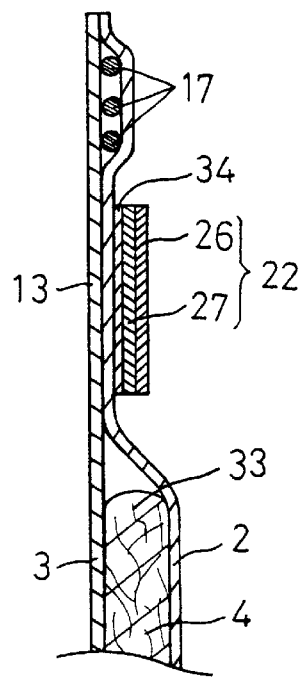
FIG. 3 is a sectional view taken along line III—III in FIG. 2.
Figure 4:
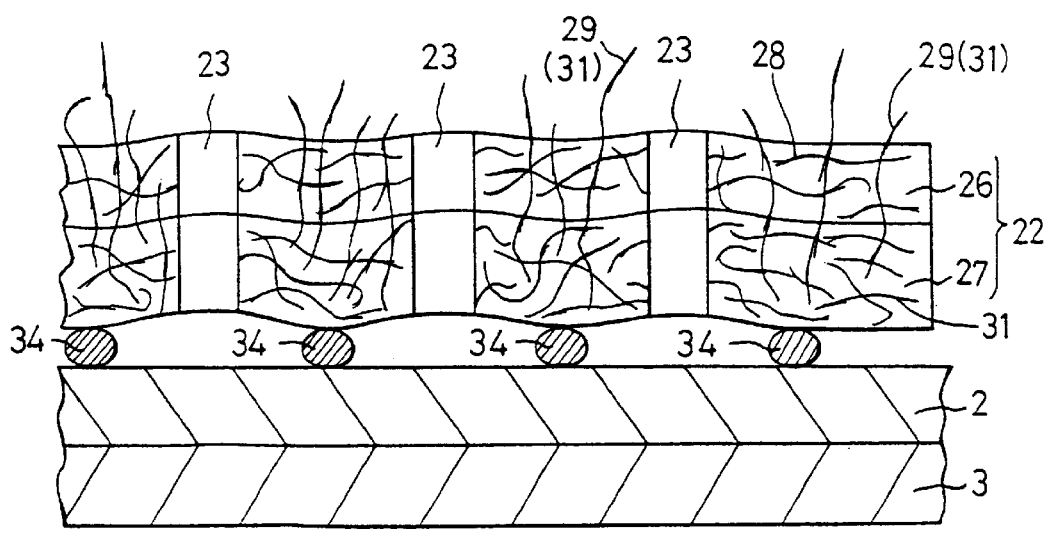
FIG. 4 is a sectional view taken along line IV—IV in FIG. 2.

FIG. 3 is a sectional view taken along a line III—III in FIG. 2 and FIG. 4 is a sectional view taken along a line IV—IV in FIG. 2 in a scale larger than in FIG. 3. The rear sweat-absorbent sheet 22 comprises an inner layer 26 destined to come in contact with wearer's skin and an outer layer 27 lying on the side opposed to the inner layer 26. The inner layer 26 consists of hydrophobic fibers 28 of 70~98 w % and hydrophilic fibers 29 of at least 2 w % with a basis weight of 5~50 g/m$^2$. The outer layer 27 consists of hydrophilic fibers 31 of 50~100 w % with a basis weight of 5~100 g/m$^2$. Ratio of the basis weight between the inner layer 26 and the outer layer 27 is in a range of 1:1~1:20. The hydrophilic fibers 29 forming the inner layer 26 preferably include hydrophilic fibers 31 extending from the outer layer 27 through interstices of the hydrophobic fibers 28 forming the inner layer 26 to wearer's skin. More preferably, most of the hydrophilic fibers 29 are those hydrophilic fibers 31 extending from the outer layer 27 in the manner as has been described just above. These inner and outer layers 26, 27 are combined into one by mechanically intertwining these fibers 28, 29, 31. The mechanical intertwinement of these fibers 28, 29, 31 so that the hydrophilic fibers 31 of the outer layer 27 may partially extend from the outer layer 27 into the inner layer 26 is achieved by a process as will be described. Namely, second fibrous web destined to form the outer layer is placed upon first fibrous web destined to form the inner layer 26 on a mesh-like support and these two fibrous webs are then subjected to high pressure columnar water streams ejected from above the second fibrous web. It is also possible to bond the inner and outer layers 26, 27 together using suitable adhesive such as hot melt adhesive or fusing the fibers 28, 29, 31 together.

The rear sweat-absorbent sheet 22 is preferably breathable through the interstices of the fibers 28, 29, 31 forming the inner and outer layers 26, 27. To improve the breathability of this sweat-absorbent sheet 22, it is possible to form a plurality of vent pores 23 extending through both the inner and outer layers 26, 27. Each of these pores 23 may have a diameter of 0.5~5 mm and totally occupy 2~50% of a total surface area of the rear sweat-absorbent sheet 22.

Such rear sweat-absorbent sheet 22 has its outer layer 27 circumferentially extends on the end flap 13 of the rear waist region 7 between the end 33 of the core and the elastic member 17 associated with the waist-opening and bonded to the inner surface of the end flap 13 by means of hot melt adhesive 34. Preferably, the sheet 22 is bonded to the inner surface of the end flap 13 intermittently in the circumferential direction to prevent a desired stretchability of the elastic member 17 from being affected by the presence of the sheet 22. Bonding of the rear sweat-absorbent sheet 22 to the end flap 13 may be achieved by means of hot melt adhesive 34 as in the illustrated case or by fusion of the sweat-absorbent sheet 22 with the end flap 13. The sweat-absorbent sheet 22 bonded to the end flap 13 in this manner neither affects the stretchability of the elastic member 17 associated with the waist-opening nor covers the core 4 since the sheet 22 is placed to be spaced apart from the core 4. In this manner, it is not apprehended also that the sheet 22 might affect body fluid absorption by the core 4 through the topsheet 2.

The respective inner surfaces 26 of both the front sweat-absorbent sheet 21 and the rear sweat-absorbent sheet 22 reliably come in contact with wearer's waist as the diaper 1 provided with these sweat-absorbent sheets 21, 22 formed in the manner as has been described above is put on the wearer's body. The skin side of the inner layer 26 has a large quantity of hydrophobic fibers 28 and a small quantity of hydrophilic fibers 29 extending outward from the interstices of the fibers 28 toward wearer's skin. Consequently, an amount of sweat secreted from wearer's front and rear waist zones is absorbed by the hydrophilic fibers 29 and transferred to the outer layer 27 so that the surface contacting wearer's skin comprising the hydrophobic fibers 28 containing substantially no sweat. obviously, the outer layer 27 wetted with sweat is protected by the hydrophobic fibers 28 of the inner layer 26 from directly contacting wearer's skin. As a result, the diaper according to this invention allows the front and rear end flaps 12, 13 to be brought in close contact with the wearer's front and rear waist zones, respectively, without any anxiety that the waist zones might be stuffed with sweat. In this way, the front and rear waist zones are always kept in dried condition. The front and rear sweat-absorbent sheets 21, 22 which are breathable, particularly provided with the vent pores 23 are further effective to prevent stuffiness generated in the wearer's front and rear waist zones.

Figure 5:
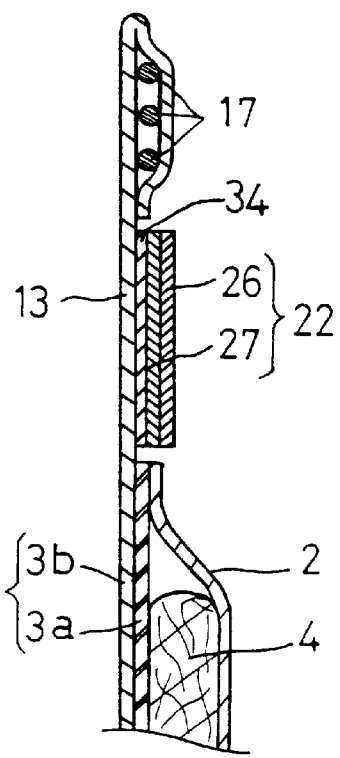
FIG. 5 is a view similar to FIG. 3 showing one preferred embodiment of this invention.

FIG. 5 is a view similar to FIG. 3 showing another embodiment of this invention. In the case of this diaper 1, the backsheet 3 comprises an inner liquid-impervious sheet 3a made of plastic film and an outer breathable sheet 3b. The breathable sheet 3b extends outward beyond the liquid-impervious sheet 3a both in the front and rear waist regions 6, 7 to form the front and rear end flaps 12, 13. It should be understood that FIG. 5 shows only the rear trunk region 7. The front and rear sweat-absorbent sheets 21, 22 are bonded to the breathable sheet 3b around the trunk regions by means of adhesive 34 applied intermittently in the circumferential direction and the front end flap 12 as well as the rear end flap 13 are breathable in the direction of their thickness. Such unique arrangement of this diaper 1 is effective to prevent stuffiness possibly occurring in the wearer's front and rear waist zones. The breathable sheet 3b is preferably formed with nonwoven fabric made of hydrophobic fibers.

Figure 6:
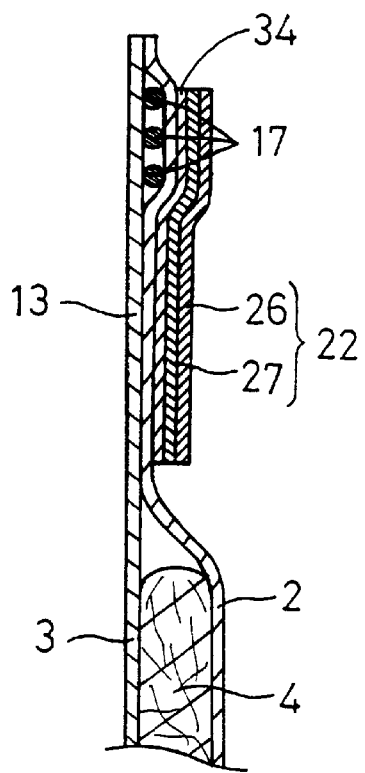
FIG. 6 is a view similar to FIG. 3 showing another preferred embodiment of this invention.

FIG. 6 is also a view similar to FIG. 3 showing still another embodiment of this invention. In the case of this embodiment, the rear sweat-absorbent sheet 22 is dimensioned to be relatively wide and bonded to the rear end flap 13 so as to cover the elastic member 17 associated with the waist-opening. In view of a fact that the region of the wearer's body in which the diaper 1 destined to be brought under the action of the elastic member 17 in close contact with wearer's skin apt to be wetted with sweat, it is desired for the sweat-absorbent sheet 22 to absorb sweat as rapidly as possible.

It is also possible without departing form the scope of this invention to eliminate one of the front and rear sweat-absorbent sheets 21, 22. Specifically, only one of the waist regions 6 or 7 maybe provided with only the sweat-absorbent sheet 21 or 22, instead of providing both the front and rear waist regions 6, 7 with the front and rear sweat-absorbent sheets 21, 22, respectively. While this invention has been described with respect the open-type disposable diaper as a specific embodiment, this invention is applicable also to the other disposable undergarment such as a pants-type disposable diaper, disposable training pants for babies or disposable pants for children and adults. It is not essential how the liquid-absorbent core is attached to the undergarment or whether the liquid-absorbent core is attached to the undergarment or not. The hydrophobic fibers 28 may be short or long fibers of thermoplastic synthetic resin and the hydrophilic fibers 29, 31 may be pulp fibers, rayon fibers, cotton fibers, or short fibers of thermoplastic synthetic resin appropriately treated to become hydrophilic.

The disposable undergarment according to this invention is provided on the inner side of the waist-opening peripheral edge with the sweat-absorbent sheet comprising the inner layer mainly made of hydrophobic fibers and the outer layer mainly made of hydrophilic fibers. The surface of the inner layer in this sweat-absorbent sheet destined to come in direct contact with wearer's skin contains the hydrophilic fibers extending from the outer layer. Such unique construction enables the amount of sweat secreted around the wearer's waist zone to be transferred from the inner layer to the outer layer. In this way, The surface of wearer's skin can be always kept in a comfortable dried state.

What is claimed is:

1. A disposable undergarment comprising:
   a covering member having a crotch region, a front waist region, a rear waist region, and transversely opposed side edges which are connected together to as to form a waist-opening having a peripheral edge and a pair of leg-openings; and
   a sweat-absorbent sheet provided inside of said peripheral edge of said waist-opening and located exclusively in an upper portion of at least one of said front waist region and said rear waist region, said sweat-absorbent sheet comprising:
   an inner layer for contacting with a wearer's skin; and an outer layer opposed to the inner layer, said inner layer containing about 70 to about 98 wt. % of hydrophobic fibers and at least 2 wt. % of hydrophilic fibers and said outer layer containing about 50 to about 100 wt. % of hydrophilic fibers with a portion of said hydrophilic fibers in said outer layer extending outward from said outer layer through interstices of said hydrophobic fibers of said inner layer to a skin contacting surface of said inner surface.

2. The disposable undergarment according to claim 1, wherein a ratio of basis weight between said inner and outer layers is in a range of about 1:1 to about 1:20.

3. The disposable undergarment according to claim 1, wherein said covering member comprises a liquid-impervious sheet, and said disposable undergarment further comprises an absorbent core provided inside said liquid-impervious sheet, and a liquid-pervious sheet covering said absorbent core, said absorbent core extending across said crotch region into said front and rear waist regions, said absorbent core having longitudinally opposite ends, outside of at least one of which longitudinal opposite ends, said sweat-absorbent sheet is attached to an inner side of said peripheral edge of said waist-opening.

4. The disposable undergarment according to claim 1, wherein a circumferentially extending elastic member is attached under tension to said peripheral edge of said waist-opening and said sweat-absorbent sheet is attached to an inner side of said peripheral edge of said waist-opening below said elastic member.

5. The disposable undergarment according to claim 1, wherein said waist-opening's edge includes a breathable sheet.

6. The disposable undergarment according to claim 1, wherein said sweat-absorbent sheet is breathable.

7. The disposable undergarment according to claim 1, wherein a circumferential extending elastic member is attached under tension to said peripheral edge of said waist-opening and said sweat-absorbent sheet is attached to an inner side of said peripheral edge of said waist-opening so that said sweat-absorbent sheet covers said elastic member.

8. A disposable undergarment comprising:

a covering member having a crotch region, a front waist region, a rear waist region, and transversely opposed side edges which are connected together to as to form a waist-opening having a peripheral edge and a pair of leg-openings; and a sweat-absorbent sheet provided inside of said peripheral edge of said waist-opening, said sweat-absorbent sheet comprising:

an inner layer for contacting with a wearer's skin; and an outer layer opposed to the inner layer, said inner layer containing about 70 to about 98 wt. % of hydrophobic fibers and at least 2 wt. % of hydrophilic fibers and said outer layer containing about 50 to about 100 wt. % of hydrophilic fibers with a portion of said hydrophilic fibers in said outer layer extending outward from said outer layer through interstices of said hydrophobic fibers of said inner layer to a skin contacting surface of said inner surface, wherein a circumferential extending elastic member is attached under tension to said peripheral edge of said waist-opening and said sweat-absorbent sheet is attached to an inner side of said peripheral edge of said waist-opening so that said sweat-absorbent sheet covers said elastic member.

* * * * *